United States Patent [19]

Francis

[11] Patent Number: 5,099,118
[45] Date of Patent: Mar. 24, 1992

[54] DUAL SENSOR SCANNER FOR MEASURING WEIGHT OF PAPER AND RELATED SHEET PRODUCTS

[76] Inventor: Kenneth E. Francis, 21837 NE. Allworth Rd., Battleground, Wash. 98604

[21] Appl. No.: 707,617

[22] Filed: May 30, 1991

[51] Int. Cl.⁵ .................. G01N 23/00; G01N 21/35
[52] U.S. Cl. .................. 250/308; 250/358.1; 250/359.1; 250/360.1
[58] Field of Search ............... 250/360.1, 369.1, 358.1, 250/308

[56] References Cited

U.S. PATENT DOCUMENTS

| | | | |
|---|---|---|---|
| 4,289,964 | 9/1981 | Baker | 250/308 |
| 4,845,730 | 7/1989 | Mercer | 378/53 |
| 4,943,721 | 7/1990 | Vidrine, Jr. | 250/308 |

Primary Examiner—Constantine Hannaher
Attorney, Agent, or Firm—Klarquist, Sparkman, Campbell, Leigh & Whinston

[57] ABSTRACT

A dual sensor scanner includes an optical sensor and a nuclear sensor such as a beta gauge for sensing the basis weight or other parameters of paper as it is being produced by a paper making machine. The nuclear sensor signal is filtered to pass a low frequency portion and the optical sensor is filtered to pass a high frequency portion. The two filtered signals are combined to provide a substantially full frequency signal indicative of the basis weight of the paper. The sensor signals may be manually calibrated or, preferably, the nuclear sensor signal may be used to provide continuous on-line calibration of the optical sensor signal.

20 Claims, 11 Drawing Sheets

DUAL SENSOR SCANNER FOR MEASURING WEIGHT OF PAPER AND RELATED SHEET PRODUCTS

BACKGROUND OF THE INVENTION

This invention relates generally to apparatus for making material such as paper and the like. More particularly, this invention relates to a method and apparatus for measuring the paper basis weight or other parameters to make either cross directional or machine directional adjustments in the paper thickness.

In a typical process for making paper and related sheet products, a headbox is provided for receiving and containing a mixture of cellulose fiber and water. The contents are discharged through a slice lip on the headbox onto a moving wire to form a web of sheet material. In the process of making paper from this material web, maintaining an optimal basis weight is desired. Basis weight is defined as the total weight of the material per unit area, and is usually stated in grams per square meter. The basis weight of the material is a function of the cellulose flow rate into the headbox, the gap of the slice lip through which the mixture passes onto the wire and the wire speed. A stock valve between the headbox and a cellulose source controls the cellulose flow rate, while slice lip actuators control the slice lip gap.

Basis weight has traditionally been determined with nuclear (radioactive isotope) -based sensors that measure the attenuation of incident radiation, X-rays, beta rays, etc. through the paper web. The nuclear sensor, because of its cost and safety concerns, is usually a single sensor mounted for scanning back and forth across the width of the web (cross direction), rather than a number of stationary sensors aligned in the cross direction. The information gathered in each scan is processed and saved in a computer memory as a series of data boxes, each box representing a defined cross web position. For example, if the width of the paper web is 400 inches and each data box is one inch wide, then data is gathered for the 400 data boxes with each having a known cross web position.

The mean value of the samples of information gathered in a scan across the width of the paper web as it is being pulled through the machine is the scan average. The scan average is used for machine direction control of the basis weight through control of the stock valve, which modulates the flow of cellulose fibers into the headbox. The information gathered for each data box is used for cross direction (profile) control of the basis weight through control of the slice lip actuators, which adjust the slice lip gap across the headbox. Further background information on the structure and operation of paper making machinery may be found in U.S. patent application Ser. No. 629,093 filed Dec. 17, 1990, which is hereby incorporated by reference.

Although accurate, nuclear sensors have a frequency response limit of about 200 Hz. That is, such sensors require at least 0.05 seconds to accurately measure a change in a parameter such as the paper basis weight. This presents a drawback because of the need for fast scan speeds to generate an optimum number of scan averages for machine direction control of the cellulose flow via the stock valve. The faster the scan speed, the more frequent and more accurate the control. However, the scan speed of a nuclear sensor is limited by the frequency response of the sensor as well as white noise that it generates. The white noise can be as great as 10% of a desired measurement.

For profile control, the rate of change across the width of the paper web can far exceed the frequency response of the nuclear sensor. And as in machine direction control, there exists a large band of noise in measuring the profile which severely limits the ability to accurately control the slice lip actuators to provide a desired basis weight.

Sensors that may be scanned at a faster rate, such as optical sensors, are available, but none offer the long term stability of a nuclear sensor. U.S. Pat. No. 4,289,964, for example, discloses apparatus in which a stationary beta gauge is augmented by an optical scanner. The output signal of the beta gauge in one specific alignment of the paper web is compared against the output of the optical scanner in an effort to correct for signal drift that occurs in the output of the scanner. While this method of comparing the output of the two sensors offers some improvement over a nuclear-based scanner, the output is still inaccurate. For most of the web width, the web portion scanned by the optical scanner is different from the web portion measured by the beta gauge. The portions are the same only when the optical scanner is aligned momentarily with the stationary beta gauge as the optical scanner sweeps across the sheet material.

SUMMARY OF THE INVENTION

An object of the invention, therefore, is to provide a sensing mechanism that overcomes the drawbacks of the prior art.

Another object of the invention is to provide as the sensing mechanism a dual sensor scanner that utilizes the advantages of an optical sensor and nuclear sensor without the drawbacks that each sensor alone presents.

Yet another object of the invention is to provide a method of regulating the basis weight or other parameter of a material with a single scanner.

To achieve these objects, apparatus according to the invention includes an optical sensor and a nuclear sensor mounted together to provide a signal indicative of the weight of material being made. In one aspect of the invention, the signal from the optical sensor is continuously calibrated by the signal from the nuclear sensor as both sensors sense the weight of the same portion of a material web. In another aspect of the invention, the signal of the optical sensor is filtered to pass only a selected high frequency portion thereof and the signal of the nuclear sensor is filtered to pass only a selected low frequency portion thereof. The two filtered signals are then combined to produce a substantially full frequency signal indicative of the weight of the material web.

Other aspects of the invention include unique linearization and calibration techniques that improve the accuracy of the sensor signals. Also disclosed is a multiple channel optical sensor for improving the sensing of basis weight or other parameters.

With the apparatus, a computer may compare the material weight against a target weight and in response adjust the cellulose flow rate or the slice lip to maintain a desired weight.

The foregoing and other objects, features, and advantages of the invention will become more apparent from the following detailed description of preferred embodiments which proceeds with reference to the accompanying drawings.

DESCRIPTION OF PREFERRED EMBODIMENTS

Figure 1:
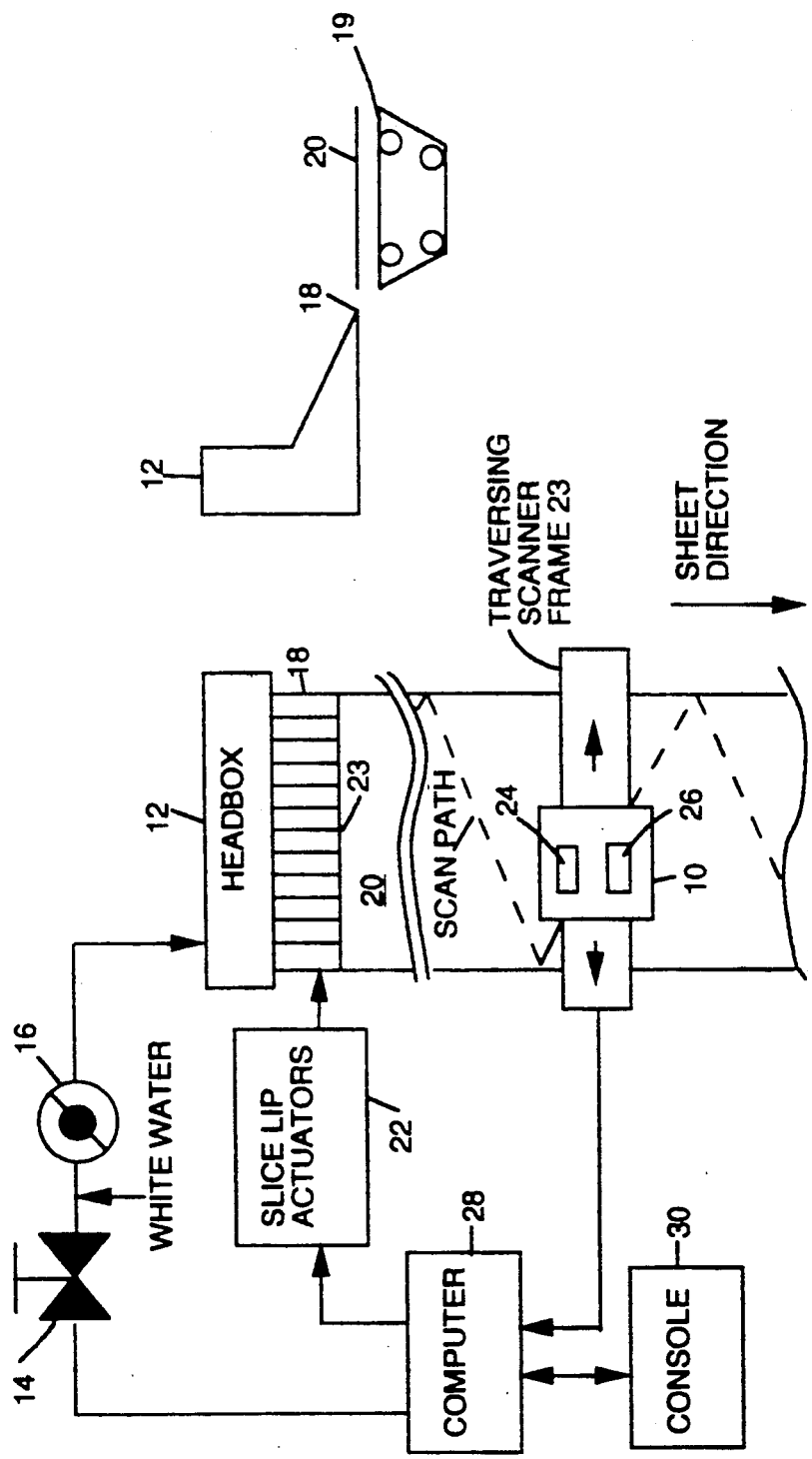
FIG. 1 is a schematic diagram of a machine illustrating a dual sensor scanner according to the invention.

FIG. 1 is a schematic diagram of a paper making machine incorporating a dual scanner 10 according to the invention. For clarity, only those portions of a paper making machine relevant to the present invention are shown. The paper making machine includes a headbox 12 which contains a watery mixture of cellulose fiber. The mixture is formed of white water recycled from the paper making process and cellulose fibers whose flow is regulated by a stock valve 14. The mixture is pumped into the headbox 12 by a fan pump 16. By regulating the flow of the cellulose fiber through the stock valve 14, the relative mixture of fiber and water is controlled and thereby the basis weight of the paper being made in the machine direction, as will be seen. Headbox 12 includes a slice lip 18 which, along with a forming board, provides a gap through which the watery mixture passes to be deposited in a moving wire 19. The moving wire causes the mixture to form a paper web 20 being pulled from the headbox in the machine direction indicated by the sheet direction arrow. The slice lip gap 18 and thus the basis weight of the paper in the cross direction is controlled by slice lip actuators 22 that regulate the slice lip gap at multiple points 23 along the slice lip 18.

The paper web exits the moving wire 19 and passes through a series of downstream wet presses (not shown) where it is further dried before passing under scanner 10. As shown in FIG. 1, scanner 10 mounts on a traversing scanning frame 23 and includes an optical sensor 24 and a nuclear sensor 26. As will be described, the optical and nuclear sensors 24 and 26 are combined in a unique fashion to sense changes in the paper basis weight at scanning speeds much greater than possible with conventional nuclear-based scanners. The sensors 24, 26 are arranged to scan the same paper web portion of the traveling sheet and are preferably arranged in alignment with the machine direction of the sheet as shown, although it is possible to align the sensors in other directions as well if desired. The scanning may be continuous or in discrete steps. Moreover, it is possible to place the scanner at a single point for stationary measurement if desired.

The output data of scanner 10 is communicated to a computer 28 that controls, among other things, the stock valve 14 and slice lip actuators 22 through various signal paths as illustrated in FIG. 1. The machine operator enters a target basis weight at a console 30 which communicates the target weight to computer 28 for comparison with the data received from the scanner 10. From that comparison, the computer seeks to maintain the target basis weight by adjusting the stock valve 14 to control the cellulose flow rate and adjusting the slice lip actuators 22 to control the slice lip gap, as will be described.

Figure 2:
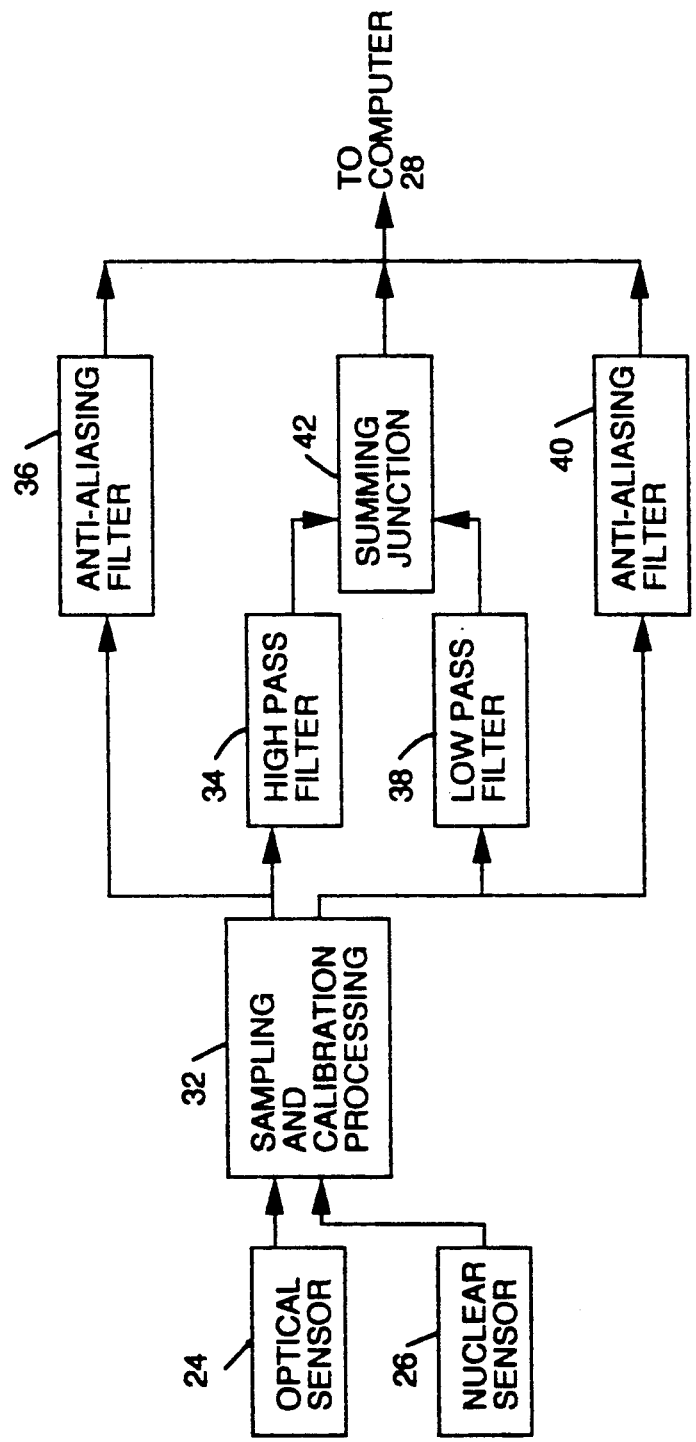
FIG. 2 is a block diagram of a dual sensor scanner according to the invention.
Figure 3:
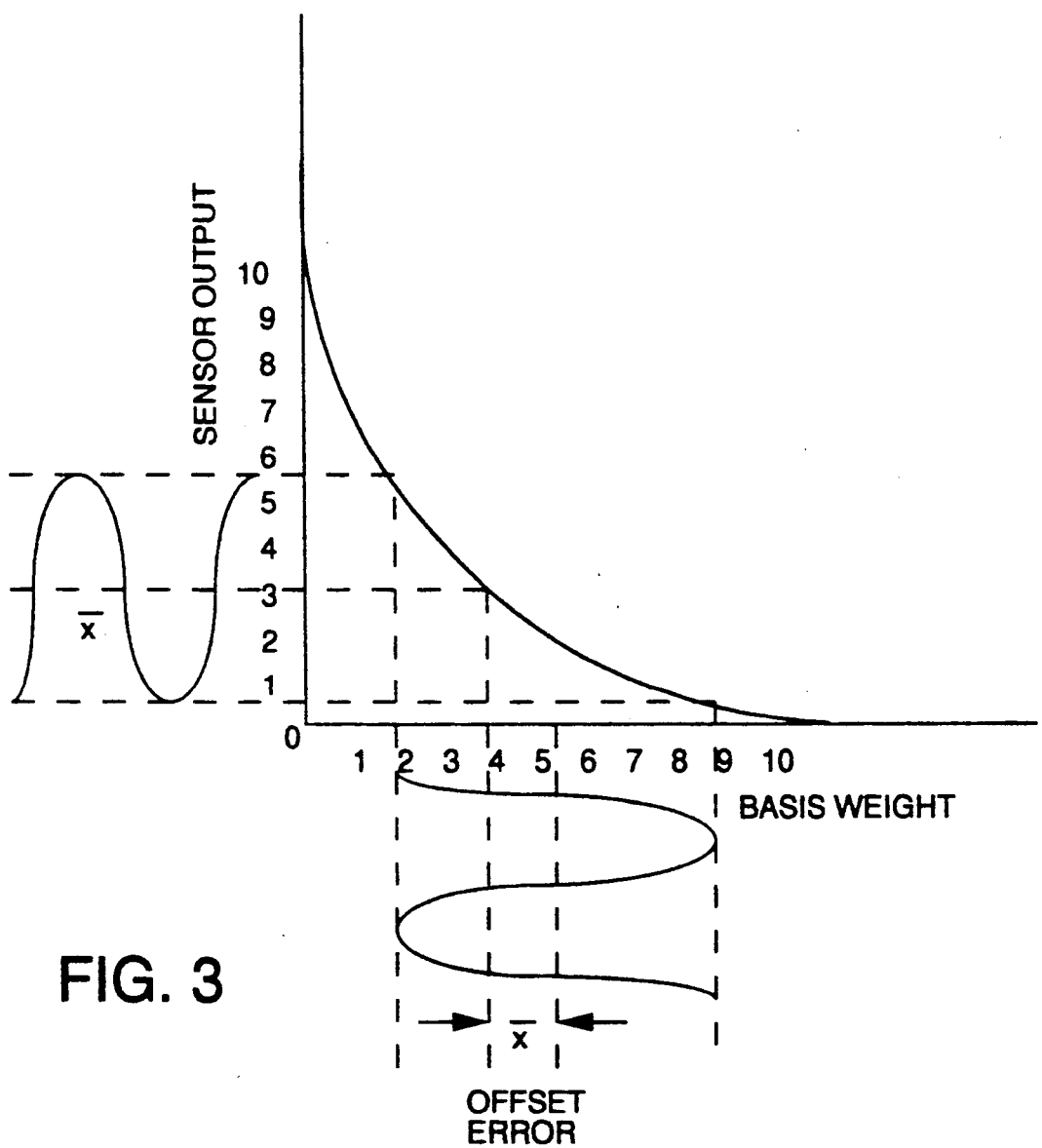
FIG. 3 is a graph showing the error that occurs in measuring basis weight if the sensor signal is not linearized.

FIG. 2 is a functional block diagram of a dual sensor scanner 10 which applies to both digital and analog embodiments to be described. At the left of the figure is the optical sensor 24 for sensing light shining through the paper web portion and generating therefrom a first signal indicative of the paper's basis weight. Adjacent to the optical sensor 24 is the nuclear sensor 26. The nuclear sensor 26 senses particles or energy passing through the paper web portion and generates therefrom a second signal also indicative of the paper's basis weight. The output signals from the two sensors are routed to a sampling and calibration processor block 32 for calibration and linearization prior to further processing. As shown in FIG. 3, the signals must be linearized to remove an offset error that otherwise occurs in translating a sensor output signal into a basis weight determination. To accomplish this, processor 32 performs one of the following calculations on the sensor signals:

$$Wt = m(\ln V) + b \tag{1}$$

$$Wt = a + b(\ln V) + c(\ln V)^2 + d(\ln V)^3 \tag{2}$$

where Wt is the linearized signal, V is the sensor signal and a,b,c,d, and m are coefficients determined in initial linearization adjustments.

Figure 4A:
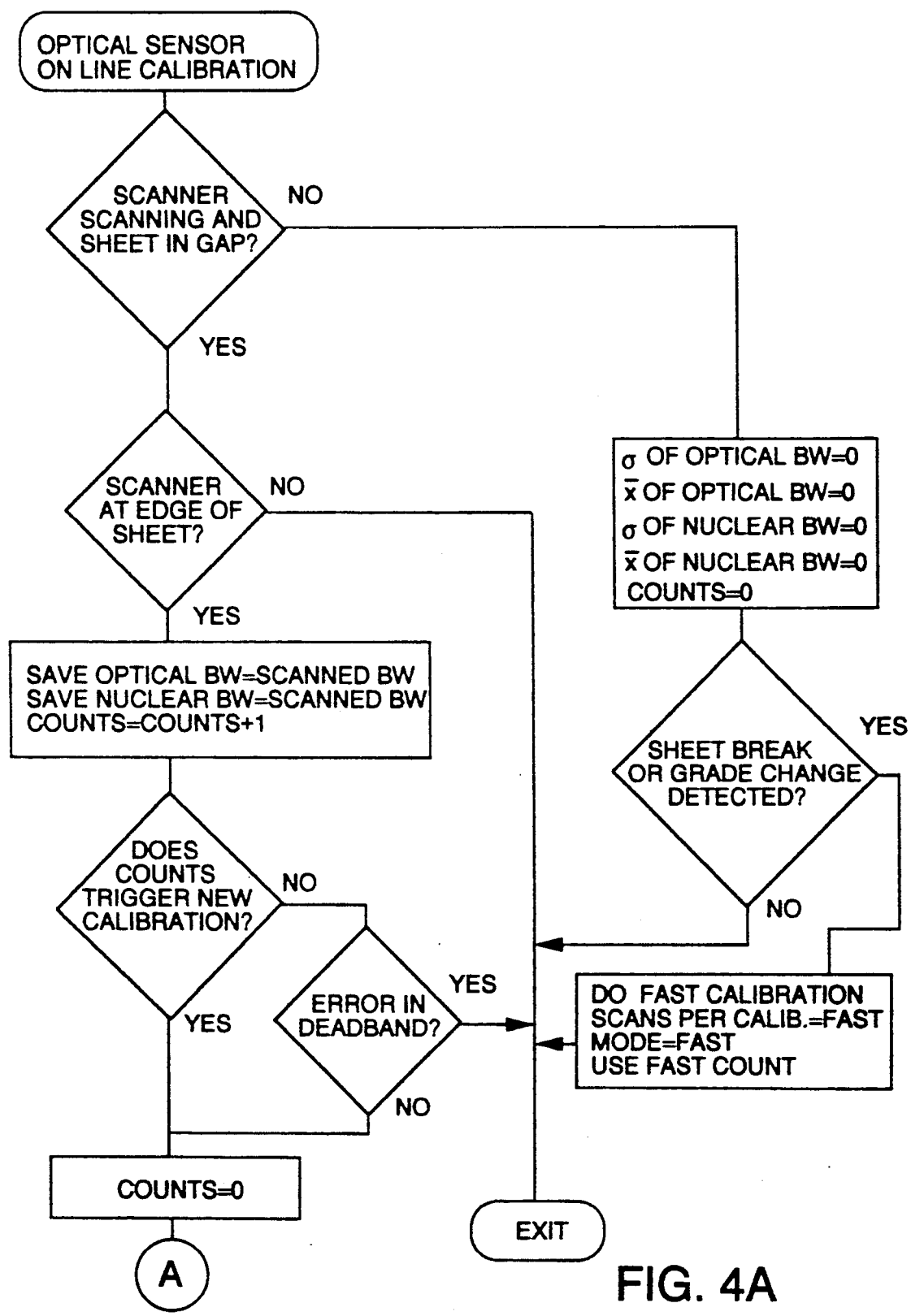
FIGS. 4A, 4B are flowcharts of the signal processing performed on the two sensor signals to calibrate the optical sensor signal to the nuclear sensor signal.
Figure 4B:
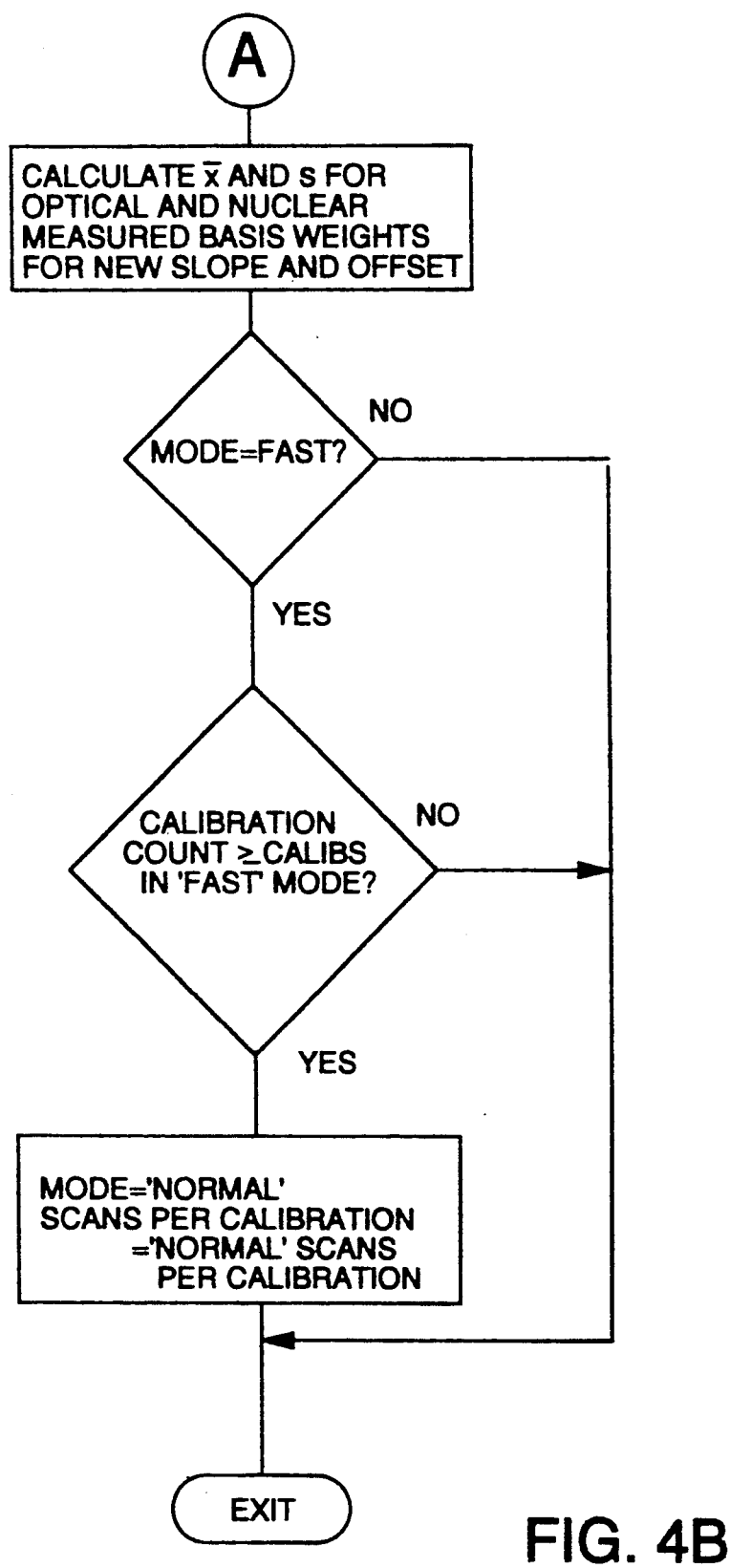

Preferably, the optical sensor signal is repeatedly calibrated to correct for signal drift that otherwise occurs over time. The method of processor 32 for on-line calibrating the optical sensor 24 is illustrated in FIGS. 4A and 4B, to be described.

The processed optical sensor signal is applied to a high pass filter 34 and to an anti-aliasing filter 36. High pass filter 34 passes only a selected high frequency portion of the processed sensor signal. In the present embodiment, all but the lowest frequencies which can be responded to by the nuclear sensor 26 are passed. By filtering the optical sensor signal in this manner, the calibration of the signal is limited to correcting for signal slope drift rather than also correcting for signal offset drift. Anti-aliasing filter 36 is included to reduce the signal response of optical sensor 24 to one half of the sampling rate of computer 28, which may be quite low to allow computer 28 to perform multiple other tasks for the paper making machine. Computer 28 utilizes the output of filter 36 to compute the average and standard deviation values for the optical-measured basis weight for use in calibration.

The processed nuclear sensor signal is applied to a low pass filter 38 and to an anti-aliasing filter 40. Low pass filter 38 passes only a selected low frequency portion of the nuclear sensor signal. In the present embodiment, the bandwidth of the filter 38 is from DC to about 2 Hz to reduce the white noise from the nuclear source. By filtering the nuclear sensor signal in this manner, the signal may be used in conjunction with the filtered optical sensor signal to provide a full frequency spectrum sensor signal. Anti-aliasing filter 40 is included to reduce the signal response of nuclear sensor 26 to one half of the sampling rate of computer 28. Computer 28 utilizes the output of filter 40 to compute the average and standard deviation values for the nuclear-measured basis weight for use in calibration.

Figure 5:
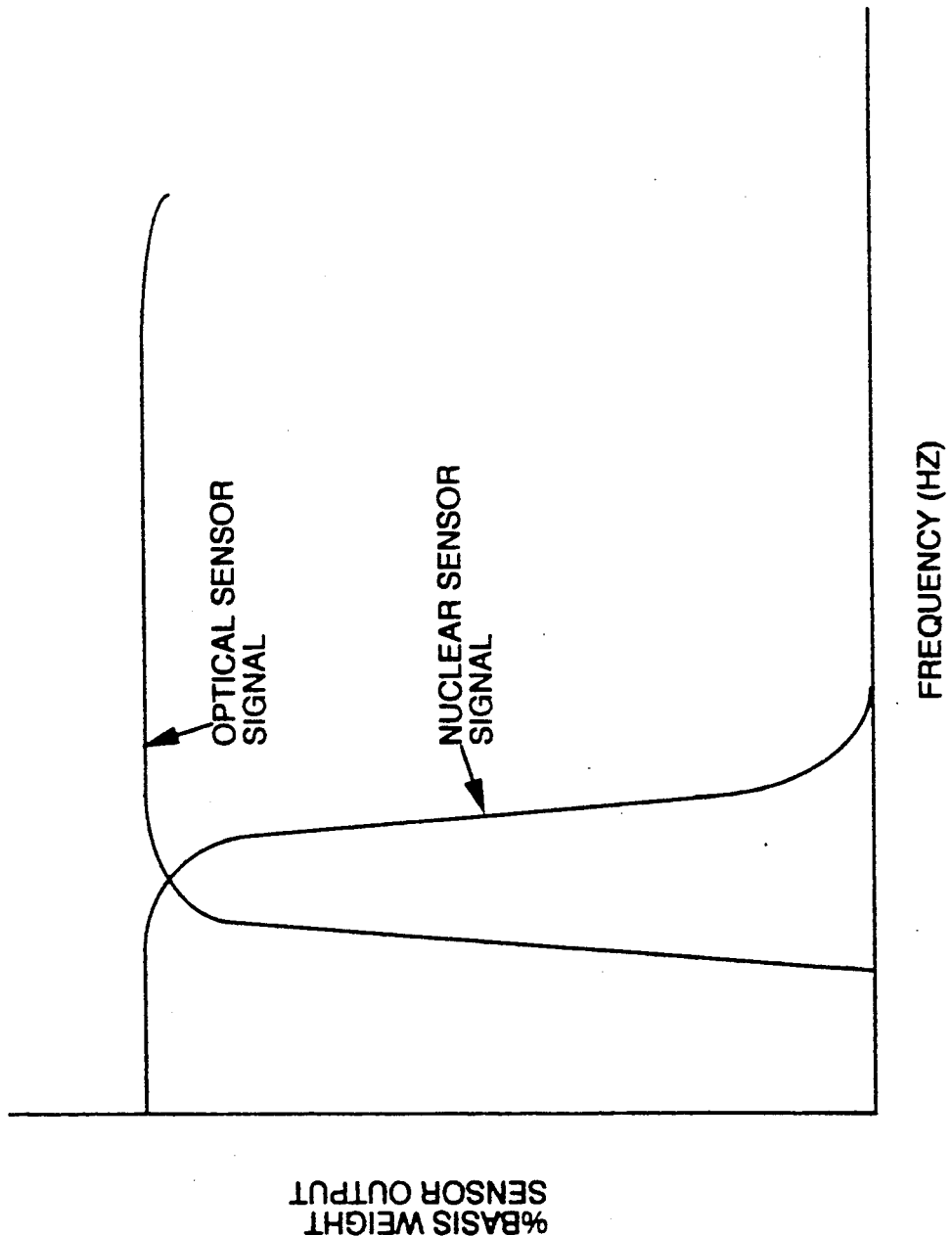
FIG. 5 is a graph of the frequency response of the dual sensor scanner, which includes the summed filtered responses of the nuclear sensor and optical sensor.

The outputs of high pass filter 34 and low pass filter 38 are summed at a summing junction 42. As shown in FIG. 5, summing junction 42 adds the high frequency portion of the optical sensor signal from filter 34 and the low frequency portion of the nuclear sensor signal from filter 38 to produce a substantially full frequency signal indicative of the basis weight of the paper web. The output of summing junction 42 along with the outputs of anti-aliasing filters 36 and 40 are routed to computer 28, which samples and compares the basis weight signal to target signals in a manner to be described.

In a digital embodiment of the scanner 10, one or more of blocks 32-40 could be carried out by a suitably programmed digital signal processing circuitry, including the sampling, calibration, linearization, filtering and summing. It may be possible with sufficiently powerful processing circuitry to incorporate the sampling function performed by computer 28 into the processing circuitry as well, eliminating the need for filters 36 and 40.

Figure 6:
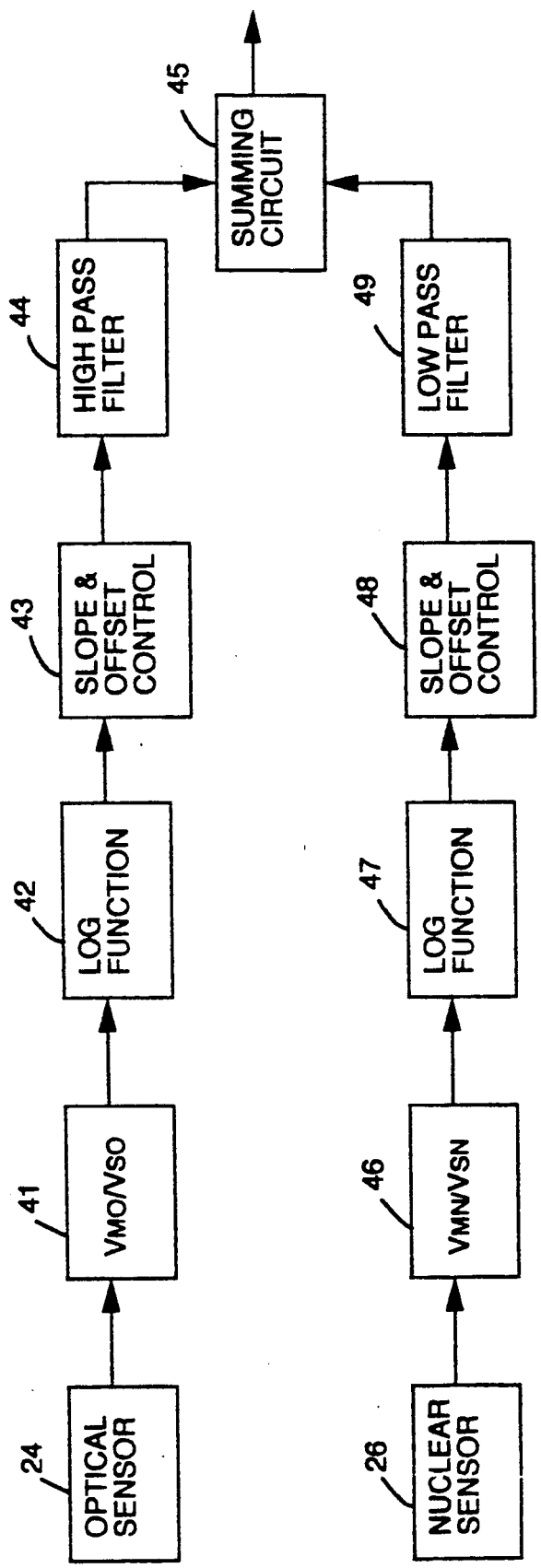
FIG. 6 is a block diagram of an analog embodiment of the dual sensor scanner of FIG. 2.

FIG. 6 is a block diagram of an analog embodiment of the dual sensor scanner of FIG. 2. The measured sensor signal $V_{mo}$ from optical sensor 24 is calibrated to a standard sensor signal $V_{so}$ with calibration circuitry 41. The calibration is done manually, but it may be possible to provide continual calibration if desired. The calibrated optical sensor signal is applied to log function circuitry 42 for linearization and then to slope and offset control circuitry 43 for calibrating the signal to desired units of measurement. Circuitry 43 also allows for manual adjustment. The sensor signal is then passed through a high pass filter 44 to a summing junction such as an amplifier circuit 45. Similarly, the measured sensor signal $V_{mn}$ from nuclear sensor 26 is calibrated to a standard sensor signal $V_{sn}$ with calibration circuitry 46. The calibration is done manually, but it may be possible to provide continual calibration if desired. The calibrated nuclear sensor signal is applied to log function circuitry 47 for linearization and then to slope and offset control circuitry 48 for calibrating the signal to desired units of measurement. Circuitry 48 also allows for manual adjustment. The sensor signal is then passed through a low pass filter 49 to summing circuit 45, where it is summed with the filtered optical sensor signal. The combined signal is then applied to computer 28 in the manner previously described.

The linearization circuitry may be omitted if the sensed signal is already sufficiently linear.

Figure 7:
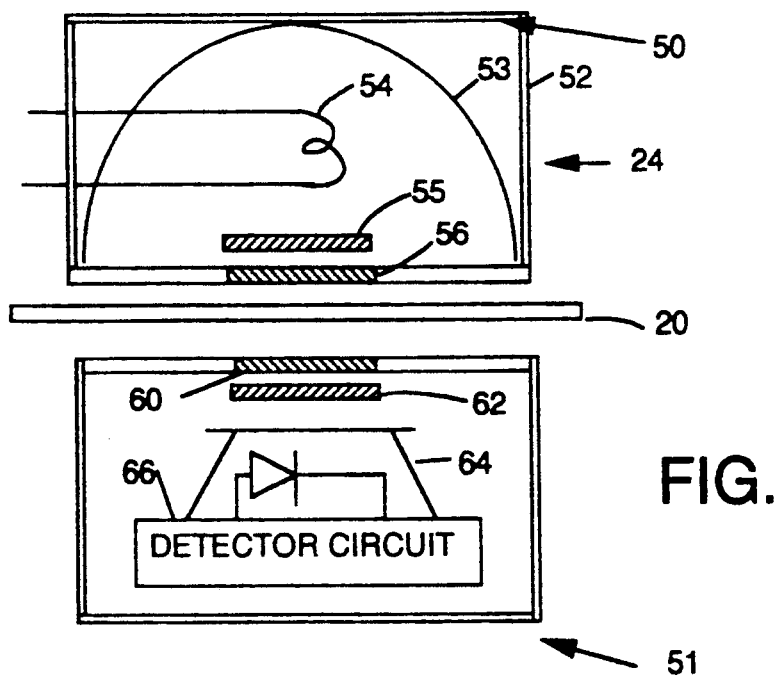
FIG. 7 is a pictorial view of an optical sensor that may be incorporated into the dual sensor scanner of FIG. 2.
Figure 7:
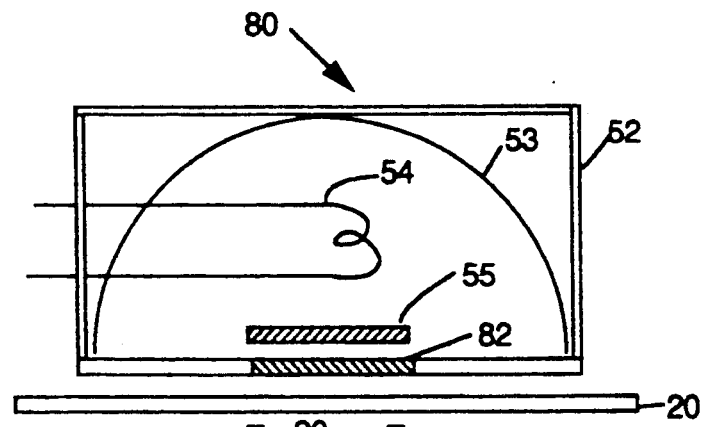

Referring to FIG. 7, optical sensor 24 includes a light source assembly 50 mounted for movement on one side of the paper web 20 and a light detector assembly 51 mounted for parallel movement on the other side of the web. The source assembly 50 includes a rugged housing 52 designed for use in a hostile environment. Housing 52 is typically sealed and charged with dry nitrogen for protecting the internal components from moisture and corrosive gases. Mounted within housing 52 is a reflector 53 for directing the optical energy from a light source 54 such as a lamp toward the paper web 20. The lamp can be any stable lamp with adequate spectral output at the desired wavelengths. Power for quartz iodine or quartz halogen lamps may be either AC or DC. In either case adequate voltage regulation is required to prevent measurement errors. If AC power is used for the lamp, it would likely be because of the need for modulating a detector within detector assembly 51. For example, a lead sulfide detector is typically modulated. For source 54, a wavelength that can be detected by a silicon photodiode is preferred, although other wavelengths are acceptable if a different detector is utilized. Wavelengths detectable by a silicon photodiode are in the range of 500 to 1200 nanometers. Photodiodes have an extremely low noise level and respond well at these wavelengths.

The light emitted by source 54 is collimated by an optical path collimator 55 that produces a beam of parallel rays of light directed toward the paper web 20. The collimation is used to control the size of the spot where the light strikes the web. Immediately adjacent to the collimator 55 is a window 56 that filters and diffuses the light from source 54. The window, filter and diffuser may be combined into a single unit, as here, or into separate units if desired. Window 56 preferably has a center wavelength at about 1000 nanometers and a band-pass of about 50 nanometers. However, the values are a matter of design choice depending on the type of paper being processed. The diffuser is not typically used for heavier weight paper since it reduces signal strength. For lighter weight paper, the diffuser is used to reduce x, y, and z sensitivity to mechanical changes between the source assembly 50 and detector assembly 51. The mechanical changes relate to mechanical instability that exists between the carriage supporting the detector assembly 51 and the carriage supporting the source assembly 50 as the sensors 24 and 26 are scanned across the paper web 20.

The light detector assembly 51 similarly includes a housing 58 and has a window 60 for receiving the unabsorbed, attenuated light from source 52 that passes through paper web 20, the degree of attenuation related to the basis weight of the paper. The received light is focused through a optical path collimator 62 onto a light detector 64 such as the silicon photodiode discussed above. In circumstances where it is desirable to measure paper with a high moisture content, a light wavelength in the range of 1450 to 1940 nanometers is required to be sensitive to the water content. The preferred detector in such circumstances is a lead sulfide detector.

Figure 8:
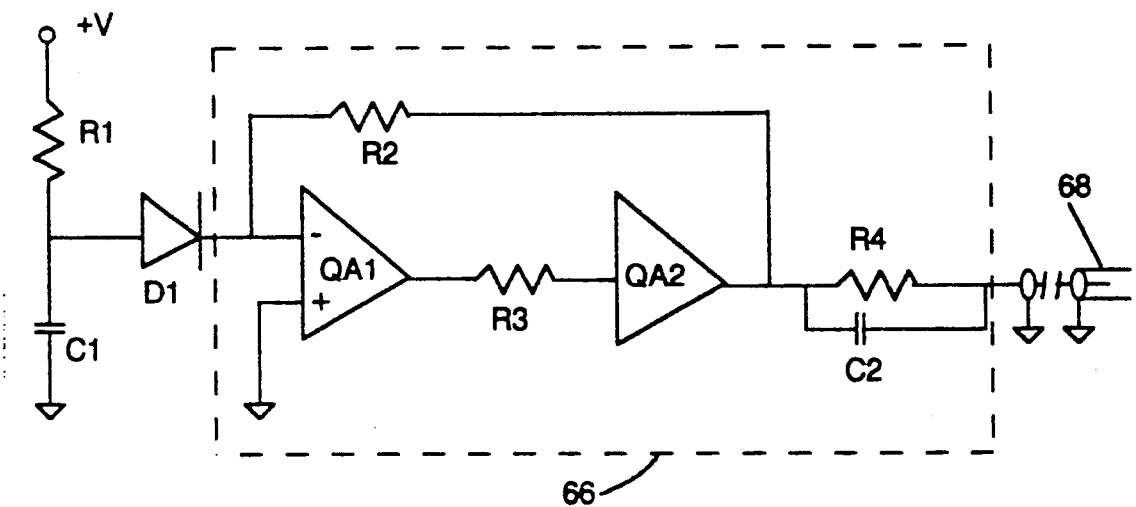
FIG. 8 is a schematic diagram of a detector circuit within the optical sensor of FIG. 7.

Referring to FIG. 8, the attenuated light sensed by detector 64 is converted into an output voltage by detector circuitry 66 so that the sensor signal can be carried by coaxial cables 68, twisted pairs, etc., to the other elements of the scanner 10, which may be located several hundred feet from the paper machine. Detector circuitry 66 includes current limiting resistor R1 and decoupling capacitor C1 for providing current to photodetector D1. When light strikes the photodetector D1, the detector provides current to current amplifier QA1 which amplifies the current signal along with current driver QA2. A feedback loop with resistor R2 provides sufficient voltage gain at the output of QA2 to drive signals through cable 68 to computer 28. To improve the frequency response of the amplified signal, it is passed through a filter comprising resistor R4 and capacitor C2 before it is applied to cable 68.

Figure 9:
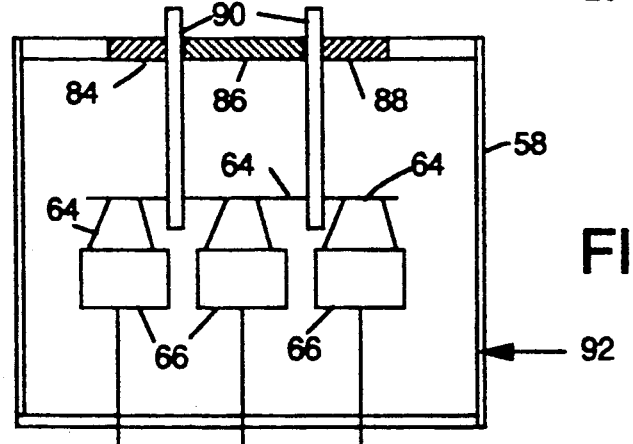
FIG. 9 is a pictorial view of a multiple channel optical sensor that may be incorporated into the dual sensor scanner of FIG. 2.
Figure 9:
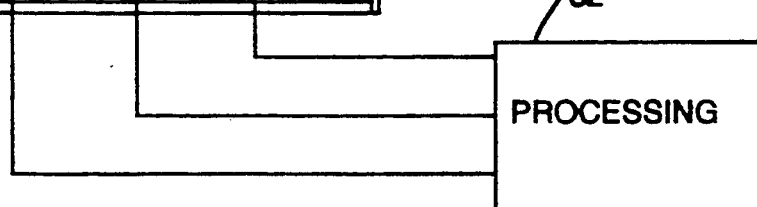

Certain recycled paper may have carbon black and large variations in sheet constituents. With this paper it may be desirable to employ a multiple channel optical sensor such as shown in FIG. 9. The multiple channels reduce errors due to composition changes in the sheet of paper and provide for better linearization. The elements of a multiple channel optical sensor are similar to those of a single channel optical sensor, except for the following differences. Within an assembly 80 a window 82 is provided that passes light in a bandwidth wide enough to cover multiple detector filters 84, 86, 88 in detector assembly 92. The multiple filters are separated by shielding 90. Shielding 90 acts as collimators for on-line measurement where same-spot, same-time measurement is not required. In circumstances where same-spot measurement is required, a beam splitter may be included to split a single beam into several beams, each then filtered separately. The single beam would first pass through a window/condenser before striking a beam splitting prism or equivalent device. It is also possible to include other, non-optical sensors in the multiple channel sensor such as ultraviolet, ultrasonic, etc., for measuring parameters such as temperature, bone-dry weight, etc.

Each detector filter 84, 86, 88 is designed to cover a nonoverlapping portion or channel of the light bandwidth passed by diffuser 82. In this way the basis weight can be calculated from different signals to ensure an accurate measurement. The light passed by each filter 84, 86, 88 is detected by a detector 64 and converted to a signal voltage by detector circuitry in the manner described. The multiple sensor signals are then routed to the processor 32 or an equivalent computing device where the measurement is made by taking into account the several signals.

Figure 10:
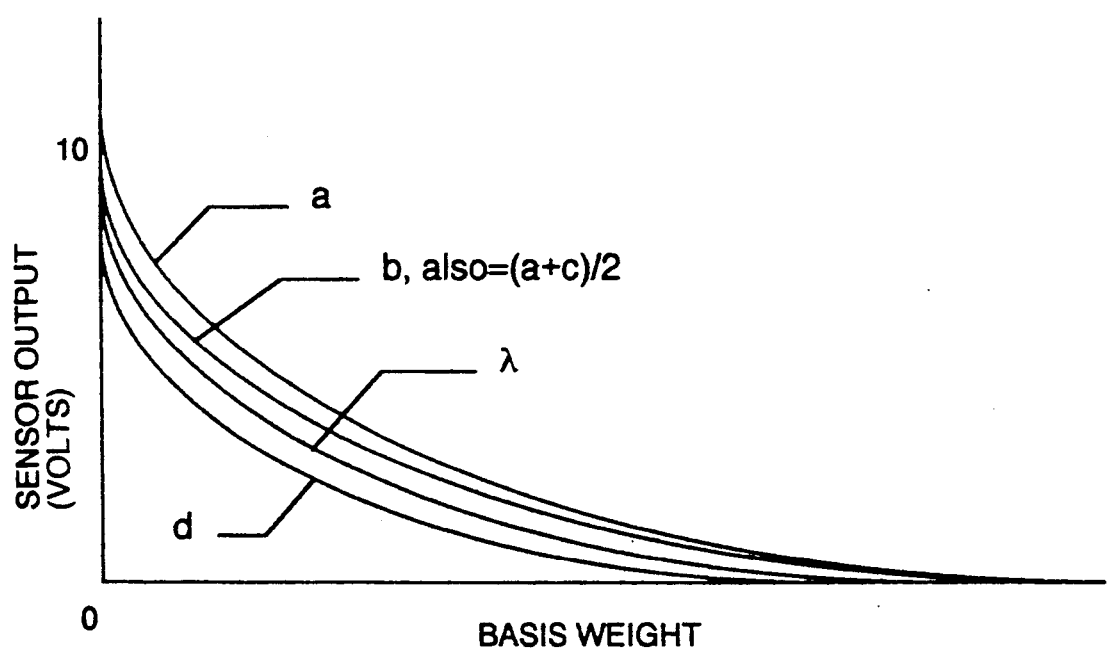
FIG. 10 is a graph illustrating the use of signals in a multi-channel sensor to determine basis weight.

Through the use of multiple channels, signals may be combined to make measurements that otherwise could not be obtained. For example, the graph in FIG. 10 illustrates how the processing of multiple signals can improve accuracy and reduce errors. Carbon black is typically present in recycled paper in ever changing amounts. The curves on the graph of FIG. 10 are defined as follows:

a = reference signal 1 and fiber condition signal 3
b = carbon black preferential absorbing frequency signal
R = reference signal 2
c = fiber condition signal 2

In this example, the two reference wavelengths are selected to have scattering/absorption signals equally balanced on both sides of the preferential absorbing frequency signal when carbon black is not present. By calculating $(a+c)/2$, however, a new absorption curve is obtained that matches curve b in the absence of carbon black. Then a ratio of $((a+c)/2)/b=1.0$ exists without carbon black present in the paper web 20. The ratio will vary directly with carbon black and can be used in the optical sensor basis weight calculation to correct for carbon black errors.

Another example would be for correction for scattering effects of optical energy due to changes in wood species, refining, fiber length, size, fluff, and blend of different kinds of paper fibers and additives. The scattering measurement that would define fiber mechanical conditions would be:

Scattering Effect = $((b+c)/2)/((a+d)/2)$

The range of calculations is not limited to the above. The way variables such as a, b, c, etc, are used to compensate for the basis weight measurement will generally be determined by the behavior of the specific grade of paper being measured. For example, tests could be run to measure the effects of carbon black on the optical sensor measurement and the results would be used to correct for errors in slope and offset.

Figure 11:
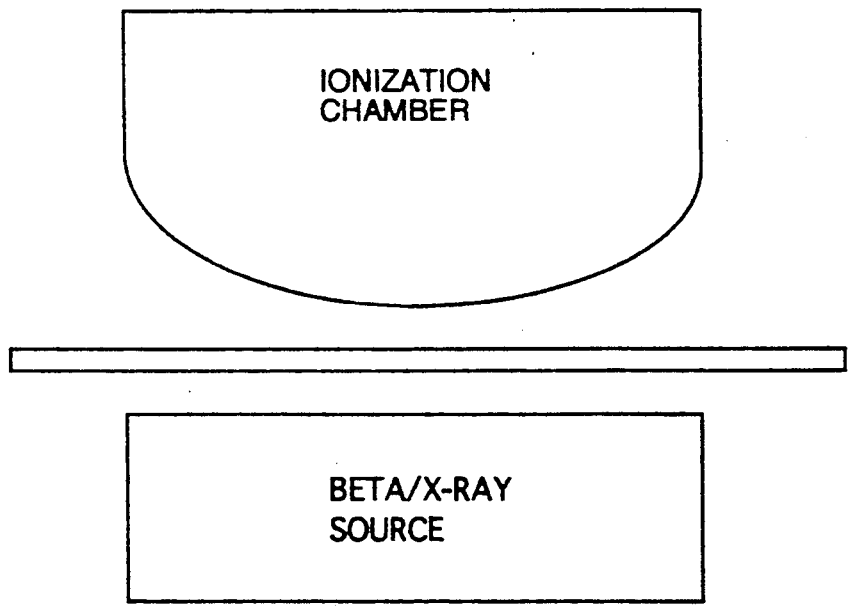
FIG. 11 is a pictorial view of a beta gauge that may be incorporated as a nuclear sensor into the dual sensor scanner of FIG. 2.

FIG. 11 shows a pictorial view of a nuclear sensor 26 that may be used in the dual sensor scanner 10. Sensor 26 includes a nuclear source 100 mounted for movement on one side of paper web 20, such as a beta particle, X-ray or equivalent source for generating particles. Mounted for parallel movement on the other side of web 20 is a particle detector 102 such as an ionization chamber for collecting particles that pass unabsorbed through the web portion.

Operation

Calibration may be manually performed as an initialization step as in the analog embodiment of FIG. 6, or preferably continuously on-line as the scanner 10 scans. On-line calibration of the optical sensor signal in a digital signal processing environment is illustrated in the flowcharts of FIGS. 4A and 4B. In a digital embodiment, the processor 32 samples the sensors' outputs at 50 to 100 kHz for performing fast linearization and calibration. It then combines the linearized and calibrated samples to obtain a basis weight. The main computer 28 then applies slope and offset values to the basis weight. These values are generated through on-line calibration of the sensors using the outputs of the filters 36 and 40 as previously described and the summing junction 42.

Referring to FIG. 4A, before a sheet is passed through the scanner 10, computer 28 (or processor 32) initializes average and standard deviation variables relating to the basis weight determinations by the two sensors 24 and 26. A "fast" calibration is then performed to provide initial settings. This calibration is performed for a number of counts, which may equal a number of scans or number of samples, as desired.

The calibration, whether fast or normal, is illustrated in FIG. 4B. The program calculates new average and standard deviation values for the optical and nuclear (beta) -measured basis weights and uses these for determining new slope and offset values for the optical sensor 24 with the following calculations:

$$A_o = \Sigma f(d)^2{}_o / \text{counts} \tag{3}$$

$$B_o = (\Sigma f d_o / \text{counts})^2 \tag{4}$$

$$C = \text{class interval} \tag{5}$$

$$\sigma_o = C/(A_o - B_o) \tag{6}$$

$$AM = \text{assumed mean} \tag{7}$$

$$\bar{X}_o = AM = (C \times (\Sigma f d_o / \text{counts})) \tag{8}$$

$$A_b = \Sigma f(d)^2{}_b / \text{counts} \tag{9}$$

$$B_b = (\Sigma fd_b/\text{counts})^2 \quad (10)$$

$$\sigma_b = C/(A_b - B_b) \quad (11)$$

$$\overline{X}_b = AM + (C \times (\Sigma fd_b/\text{counts})) \quad (12)$$

New slope$_o$ = old
slope$_o \times [(\overline{X}_b + \sigma_b) - (\overline{X}_b - \sigma_b)/(\overline{X}_o + \sigma_o) - (\overline{X}_o - \sigma_o)]$ (13)

New offset = $(\overline{X}_b + \sigma_b)$ + (new slope$_o \times (\overline{X}_o + \sigma_o -$ old offset$_o$)) (14)

In the fast mode the calibration count is lower than in the normal mode. If the calibration count has not been reached, the program exits and loops back to continue the calculations until the count is reached. At that point, the mode is changed back to "normal" and the count changes to the normal number of scans per calibration.

Upon exiting from fast calibration, the program loops back to continue the on-line calibration. When the scanner 10 is at the edge of web 20, the optical and nuclear basis weight values are saved and the calibration count is incremented. This count is compared against a target count. If the target count has not yet been reached, then the sensor error (optical measured basis weight minus nuclear measured basis weight) is checked to see if it is outside a predetermined deadband range. If not, the program exits and loops back to continue. Eventually the calibration count exceeds the target count or the error exceeds the deadband, at which point the program calculates new average and standard deviation values for the optical and nuclear measured basis weights. The calibration count is then zeroed and on-line calibration continues in the normal mode until a sheet is no longer detected, or there is a sheet break or grade change detected that would prompt a fast calibration.

Figures 12A, 12B:
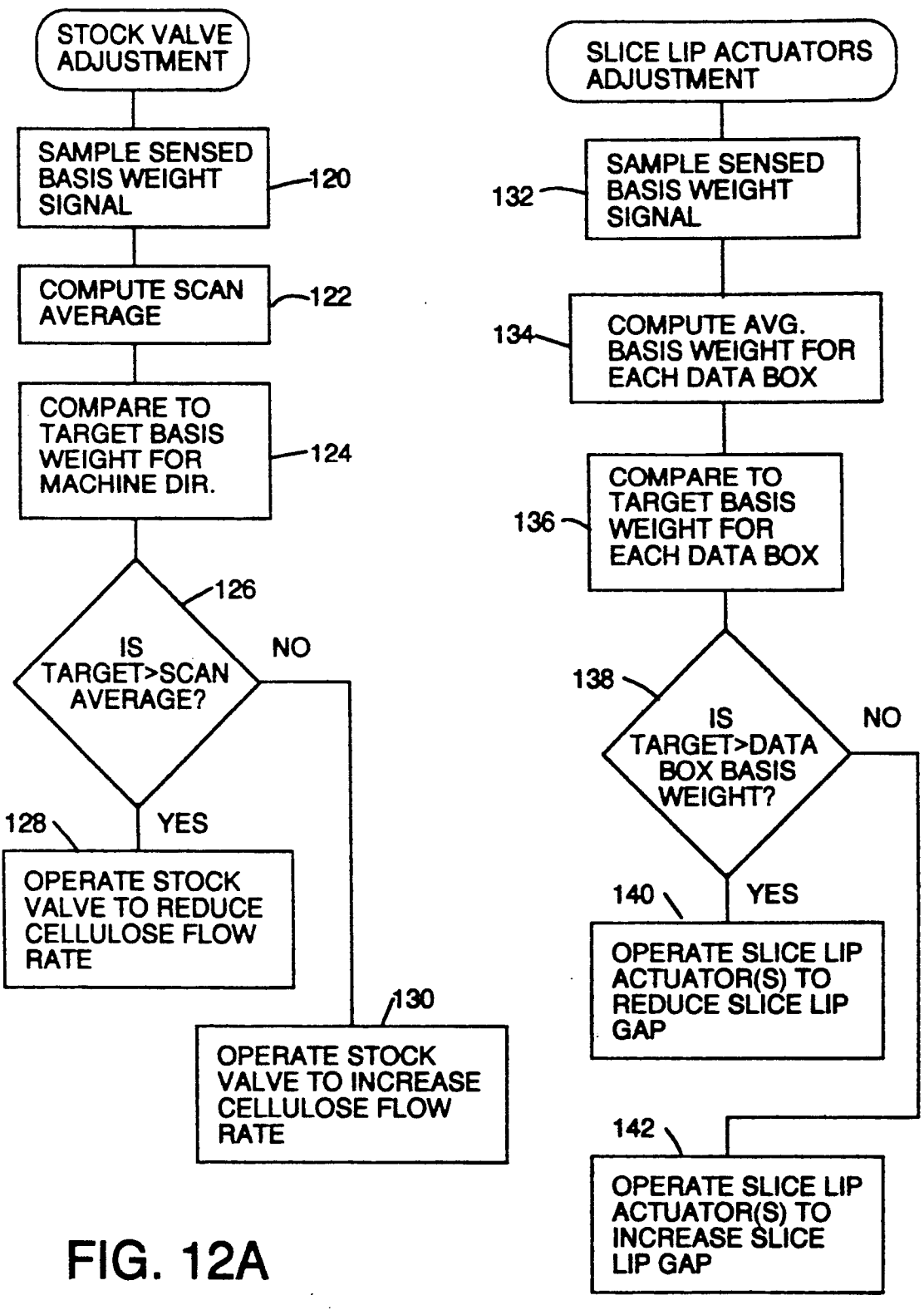
FIGS. 12A, 12B are flowcharts of methods for adjusting the stock valve and slice lip actuators to maintain a desired basis weight in the machine direction and cross direction.

The computer 28 then compares the calibrated basis weight signal form scanner 10 to a target value to adjust stock valve 14 for controlling machine direction basis weight and to adjust slice lip actuators 22 for controlling cross direction basis weight, as illustrated in FIGS. 12A and 12B. For stock valve adjustment, computer 28 samples the basis weight signal received from scanner 10 (120), computes a scan average (122), and then compares the computed scan average to a target basis weight entered by the operator (124). If the computed scan average exceeds the target weight (126), computer 28 operates the stock valve 14 through a controller (not shown) to reduce the cellulose flow rate (128) into headbox 12. If the computed scan average is less than the target weight (126), computer 28 operates the stock valve to increase the cellulose flow rate (130) into headbox 12.

For adjustment of the slice lip actuators 22, the data collected by scanner 10 is viewed differently. Computer 28 samples the basis weight signal (132), computes an average basis weight for each data box (134), and compares each computed data box average basis weight to a target data box basis weight (136). To average out machine direction variations in the paper sheet, a composite profile is developed by computing a moving average of each data box average. If the computed average data box weight exceeds the target weight (138), computer 28 operates a slice lip actuator 22 through a controller (not shown) to reduce the corresponding portion of the slice lip gap (140). If the computed data box average weight is less than the target weight (138), computer 28 operates a slice lip actuator 22 to increase the corresponding portion of the slice lip gap (142).

Having illustrated and described the principles of the invention in a preferred embodiment, it should be apparent to those skilled in the art that the invention can be modified in arrangement and detail without departing from such principles. I claim all modifications coming within the spirit and scope of the following claims.

I claim:

1. Apparatus for measuring the weight of a material, comprising:
    an optical sensor for sensing light shining through a material web portion and generating therefrom a first signal indicative of the weight;
    a nuclear sensor mounted adjacent to the optical sensor for sensing particles passing through the material web portion and generating therefrom a second signal indicative of the weight; and
    calibrating circuitry for calibrating the optical sensor signal to the nuclear sensor signal as the sensors sense the weight of the same portion of the material web.

2. The apparatus of claim 1 including:
    a high pass filter for filtering the optical sensor signal to pass only a selected high frequency portion thereof;
    a low pass filter for filtering the nuclear sensor signal to pass only a selected low frequency portion thereof; and
    a summing junction for adding the high frequency portion of the optical sensor signal and the low frequency portion of the nuclear sensor signal to produce a substantially full frequency signal indicative of the weight of the material web.

3. The apparatus of claim 2 wherein the summing junction comprising a summing circuit.

4. The apparatus of claim 1 wherein the optical sensor and the nuclear sensor are aligned with the direction of movement of the material web.

5. The apparatus of claim 1 including:
    a mount constructed for movement across the width of the material web for positioning the optical and nuclear sensors to sense the weight across the web; and
    a computer programmed to compute a scan average for an average weight across the width of the web for comparison to a target value and to compute an average for each of a plurality of data boxes representing discrete portions of the web for comparison to corresponding target values for the data boxes.

6. The apparatus of claim 1 wherein the optical sensor comprises a light source for movement on one side of the material web and a light detector for parallel movement on the other side of the web.

7. The apparatus of claim 1 wherein the optical sensor includes light of different frequencies and multiple light detectors for detecting the multiple frequencies.

8. The apparatus of claim 1 wherein the nuclear sensor comprises a beta particle source for movement on one side of the material web and an ionization chamber for parallel movement on the other side of the web.

9. An apparatus for measuring the weight of a material web, comprising:
    a first sensor having a higher frequency response for sensing the signals passing through a material web portion and generating therefrom a first signal indicative of the weight;

a second sensor mounted adjacent to the first sensor and having a lower frequency response for sensing signals passing through the material web portion and generating therefrom a second signal indicative of the weight;

a high pass filter for filtering the first sensor signal to pass only a selected high frequency portion thereof;

a low pass filter for filtering the second sensor signal to pass only a selected low frequency portion thereof; and a summing junction for adding the low frequency portion of the first sensor signal and the high frequency portion of the second sensor signal to produce a substantially full frequency scanning signal indicative of the weight of the material web.

10. The apparatus of claim 9 wherein the first sensor is an optical sensor and the second sensor is a nuclear sensor.

11. The apparatus of claim 9 including calibration circuitry for calibrating the first sensor signal and the second sensor signal.

12. The apparatus of claim 11 wherein the calibration circuitry comprises a digital signal processor.

13. The apparatus of claim 9 including linearization circuitry for linearizing the first sensor signal and the second sensor signal.

14. The apparatus of claim 9 including a computer programmed to compute a scan average for an average weight across the width of the web for comparison to a target value and to compute an average for each of a plurality of data boxes representing discrete portions of the web for comparison to corresponding target values for the data boxes.

15. A method of regulating the weight of a material in a material making process, comprising:

scanning the same portion of the material web with an optical sensor and a nuclear sensor as the material is being processed; and calibrating the optical sensor signal to the nuclear sensor signal while scanning to produce a scanning signal indicative of the weight of the material web.

16. The method of claim 15 wherein the scanning of the same portion of material web with the optical and nuclear sensors is simultaneous.

17. The method of claim 15 including:

comparing the scanning signal against a target value; and adjusting the material making process in response to the comparison.

18. The method of claim 15 including:

providing a headbox;

introducing a cellulose flow into the headbox for mixing with water to form the material;

computing from the scanning signal a scan average for the entire width of the web;

comparing the scan average against a target value; and adjusting the cellulose flow into the headbox in response to the comparison.

19. The method of claim 15 including:

providing a headbox having a slice lip gap through which the material passes;

computing from the scanning signal an average value for each of a plurality of data boxes representing discrete portions of the width of the web;

comparing each computed data box average to a corresponding target value; and adjusting a slice lip gap in response to the comparison.

20. A method of measuring the weight of paper in a paper making process, comprising:

providing a first sensor having a higher frequency response for sensing signals passing through a material web portion and generating therefrom a first signal indicative of the weight;

providing a second sensor having a lower frequency response for sensing signals passing through the material web portion and generating therefrom a second signal indicative of the weight;

sensing with both sensors the material web portion to sense its weight simultaneously with both sensors;

filtering the first sensor signal to pass only a selected high frequency portion thereof;

filtering the second sensor signal to pass only a selected low frequency portion thereof; and summing the low frequency portion of the first sensor signal with the high frequency portion of the second sensor signal to produce a substantially full frequency sensor signal indicative of the weight of the material web portion.

* * * * *

UNITED STATES PATENT AND TRADEMARK OFFICE
CERTIFICATE OF CORRECTION

PATENT NO. : 5,099,118
DATED : March 24, 1992
INVENTOR(S) : Kenneth E. Francis

It is certified that error appears in the above-identified patent and that said Letters Patent is hereby corrected as shown below:

Column 1, line 56 (specification page 2, line 16), "1990, which" should be --1990, now U.S. Patent No. 5,071,514--;

Column 10, line 36 (Amendment filed September 9, 1991, page 1), "comprising" should be --comprises--.

Signed and Sealed this

Tenth Day of August, 1993

Attest:

MICHAEL K. KIRK

Attesting Officer

Acting Commissioner of Patents and Trademarks